United States Patent
Bader

(10) Patent No.: US 6,171,264 B1
(45) Date of Patent: Jan. 9, 2001

(54) MEDICAL MEASURING SYSTEM

(75) Inventor: Gaby Bader, Gothenburg (SE)

(73) Assignee: Biosys AB, Gothenburg (SE)

(*) Notice: Under 35 U.S.C. 154(b), the term of this patent shall be extended for 0 days.

(21) Appl. No.: 09/156,667

(22) Filed: Sep. 18, 1998

(30) Foreign Application Priority Data

| May 15, 1998 | (SE) | 9801722 |
| Jun. 12, 1998 | (SE) | 9802100 |
| Jun. 12, 1998 | (SE) | 9802101 |

(51) Int. Cl.[7] .................................................. A61B 5/00

(52) U.S. Cl. .......................................... 600/595; 600/300

(58) Field of Search .................................... 600/587, 595, 600/300, 301; 340/573.1, 573.3, 573.4

(56) References Cited

U.S. PATENT DOCUMENTS

| Re. 32,180 | * | 6/1986 | Lewiner et al. | 600/595 |
| 4,274,083 | * | 6/1981 | Tomoeda . | |
| 4,771,780 | * | 9/1988 | Sholder | 600/595 |
| 5,494,046 | * | 2/1996 | Cross | 600/595 |
| 5,544,661 | | 8/1996 | Davis et al. | 128/700 |
| 5,729,205 | | 3/1998 | Kwon | 340/573 |
| 5,810,747 | * | 9/1998 | Brudny et al. | 600/595 |

FOREIGN PATENT DOCUMENTS

WO 93/16636   9/1993 (WO).

* cited by examiner

Primary Examiner—Max Hindenburg
(74) Attorney, Agent, or Firm—Nixon & Vanderhye P.C.

(57) ABSTRACT

In a medical meassuremnet system, measurements can be carried out at a distance from a hospital. Thus the patient is connected to a measuring system comprising measuring sensors and a unit for collecting data comprising a transmitter. The system also comprises a centrally located surveillance unit. The measuring sensors sense various physical and physiological parameters, for example brain activities, actions of the heart, respiration, blood pressure, blood values/tests and body movements. The sensed signals are transmitted to a portable small device of low weight for collecting and/or analyzing data, which is connected to a central surveillance unit, for example via the public switched telephone network (PSTN), a radio system, in particular a cellular radio system, or via a satellite communication. In a preferred embodiment the measuring sensors comprise a preamplifier having an identification circuit. The identification circuit is used for providing each preamplifier with a unique identity. In yet another preferred embodiment a measuring pad for measuring physical and physiological parameters is provided. The measuring pad comprises a film having piezo and/or pyro electrical characteristics, for example a PVF-film (Poly Vinyl Fluoride), or any other sensor having similar properties. By using such a film, which can convert movements into an electrical signal several advantages are achieved.

25 Claims, 2 Drawing Sheets

MEDICAL MEASURING SYSTEM

TECHNICAL FIELD

The present invention relates to a medical measuring system and in particular to a method and a system for portable measurement, surveillance, transmission recording and analysis of physical, physiological and other functions and parameters.

BACKGROUND OF THE INVENTION AND PRIOR ART

In various medical areas it is sometimes necessary to perform measurements and surveillance during long periods of time. Examples of such medical areas could be neurology, cardiology, telemedicine, long-term nursing and home nursing. During such long-term measurements, which typically last for days, the patient must at all time be connected to the measuring equipment in order for a continuous measurement to occur.

Furthermore, in most cases such measurements must be supervised by qualified personnel in order to prevent interruptions in the measurements and to check that the condition of the patient does not worsen. The latter is very important since measurements of the kind mentioned above often are included in treatment as follow-up examinations or in investigations for establishing a diagnosis. Thus, it is common that the person responsible for correctly carrying out the measurements is a doctor.

These long term measurements must therefore be carried out using ambulatory measurement equipment, since the patient can hardly be expected to remain in bed during the long periods required for obtaining a continuous series of measurements. Further, the measuring equipment must be located at a hospital in order to there be supervised by a doctor in charge.

This is of course expensive for the payer of the hospital care and not particularly comfortable for the patient who cannot leave the hospital despite the fact that he/she is not in any need of hospitalization at the movement.

SUMMARY

It is an object of the present invention to reduce the costs resulting from long-term measurements.

It is another object of the present invention to improve the environment and reduce the difficulties for patients who need to undergo long-term measurements.

It is yet another object of the present invention to provide a measuring pad for measurements of physical and physiological parameters, which is very sensitive and which therefore can be located at a fairly long distance from a patient, for example beneath a thick mattress or even under a bed.

It is a further object of the present invention to provide a pre-amplifier, which is easy to handle and which produces or eliminates the risk for erroneous handling, and which is suited to be used together with the measuring equipment.

These objects and others are obtained by means of a method and system by means of which the measurements can be carried out at a distance from a hospital. Thus the patient is connected to a measuring system comprising measuring sensors and a unit for collecting data comprising a transmitter. The unit for collecting data preferably also comprises means for performing different analyses. The system also comprises a centrally located surveillance unit.

The measuring sensors sense various physical and physiological parameters, for example brain activities, actions of the heart, respiration, blood pressure, blood values/tests and body movements. The sensed signals are transmitted to a portable small device of low weight for collecting and/or analysing data, which is connected to a central surveillance unit, for example via the public switched telephone network (PSTN), a radio system, in particular a cellular radio system, or via a satellite communication. The central surveillance unit is monitored by qualified personnel which can follow the measurements and also in certain cases reprogram the unit for collecting and analysing data during an ongoing measurement.

In a preferred embodiment the measuring sensors comprise a preamplifier having an identification circuit. The identification circuit is used for providing each preamplifier with a unique identity. The fact that each preamplifier is given a unique identity makes it possible for the unit collecting and analysing data to automatically check if the correct pre-amplifier has been attached to the correct input terminal and, if that is not the case, either correct the error or give a signal indicating that an erroneous connection has been made.

In yet another preferred embodiment a measuring pad for measuring physical and physiological parameters is provided. The measuring pad comprises a film having piezo and/or pyro electrical characteristics, for example a PVF-film (Poly Vinyl Fluoride), or any other sensor having similar properties. By using such a film, which can convert movements into an electrical signal several advantages are achieved. Thus, a measuring pad comprising such a film is easy to fold together and can be made very sensitive, whereby it can be placed beneath the mattress or even under the bed in which the patient is lying.

Furthermore, the signals transmitted to/from the central surveillance unit can be image/video signals (if a camera is connected to the system), audio signals (such as speech), text signals (for transmission of prescriptions etc.) as well as biological signals. In this manner the personnel at the surveillance end of the system can have full access to information required for providing the patient with proper medical treatment at distance.

The use of the system as described herein provides a number of advantages compared to the prior art. Thus, the patient no longer needs to be in a hospital but can instead be at home or at an another suitable location. Hence, by using the system the cost for hospital care is reduced or eliminated. Furthermore the patient can move around freely due to the fact that the measuring system and auxiliary equipment used for collecting data are made small and of low weight.

BRIEF DESCRIPTION OF THE DRAWINGS

The present invention will now be described more in detail and with reference to the accompanying drawings, in which.

DETAILED DESCRIPTION

Figure 1:
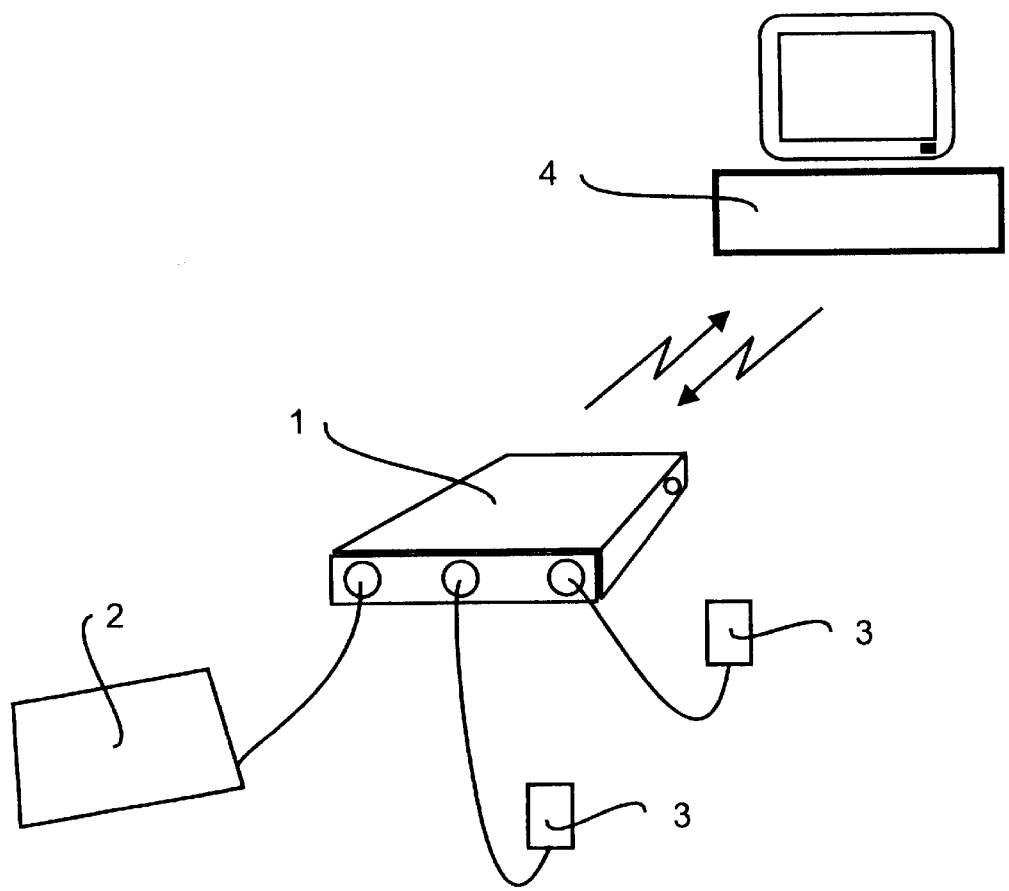
FIG. 1 is a schematic view of an ambulatory medical measuring system.

In FIG. 1 a schematic diagram of an ambulatory medical measuring system is shown. Thus a unit 1 for collecting and analysing data is connected to a measuring pad 2 and a preamplifier 3. The measuring pad 2 and the preamplifiers 3 sense different physical and physiological parameters and are described in more detail below in conjunction with FIG. 3 and FIG. 4. These signals are transmitted to the unit 1 for collecting and analysing data.

In the unit 1 the signals provided by the measuring pad 2 and the preamplifiers 3 are AID-converted and stored and analyzed. The digital data stored in the unit 1 can then be output from the unit 1 to an external computer 4.

The transmission of data to the external computer 4 can be carried out in a number of different ways. In a preferred embodiment the transmission is carried out using an infrared IR-interface. Such an arrangement has the advantage that the patient can be connected to the measuring equipment when data is transmitted from the unit 1 to the computer 4 without being physically connected to the computer 4. Thus, the risk for electrical current to be transmitted from the computer 4 to the patient is eliminated.

In another preferred embodiment the unit 1 is also provided with, e.g., a PCMCIA-card or PC-card or a similar device by means of which the unit 1 can connect to a telephone or data network. The computer 4 then does not need to be in the same room as the unit 1 when data is transmitted from the unit 1 to the computer 4. For example, the unit 1 can be located together with the patient at home and the computer 4 can be located at the hospital.

A doctor or another qualified person at the hospital can then connect to the unit 1 at any time and transmit measurements data from the unit 1 via for example the public switched telephone network or a cellular network to the computer 4. In such an arrangement the patient does not need to be disturbed or even know about when the unit 1 transmits data and must hence not be bothered by this.

In yet another preferred embodiment the unit 1 can in itself analyze the collected measurement data. Examples of analyses which the unit 1 can perform are comparisons between measured signals and threshold values corresponding to such signals.

Thus, an alarm can be activated in the unit 1 if such a threshold value is crossed either from above or from below and the computer 4 can be automatically contacted via the telephone or data network in order for the doctor or qualified personnel monitoring the computer 4 to immediately have access to all measurement data, in particular the data causing the triggering of the alarm.

In this manner an important event in the series of measured data can be spotted quickly, transmitted and possibly taken care of. For example, the information transmitted can form the basis for moving the patient to a hospital in order to perform more thorough investigations and tests or that an emergency alarm is issued and that actions required are performed.

Another advantage achieved with such an arrangement is that it is possible to perform adjustments in the settings at distance. Thus, if the doctor or qualified personnel for one reason or another wants to measure some another physical or physiological parameter, which at present is not being measured, information thereof can be transmitted from the computer 4 to the unit 1 and collection of the new desired parameter can start in the unit 1.

In yet another preferred embodiment data regarding the patients earlier conditions and possible treatment can also be stored and transmitted to/from the unit 1. The unit 1 may also be equipped with a GPS-navigation system for continuous surveillance of the movements of the patient and in order to locate the patient quickly in the case an alarm signal is transmitted and the patient must be located quickly.

Figure 2:
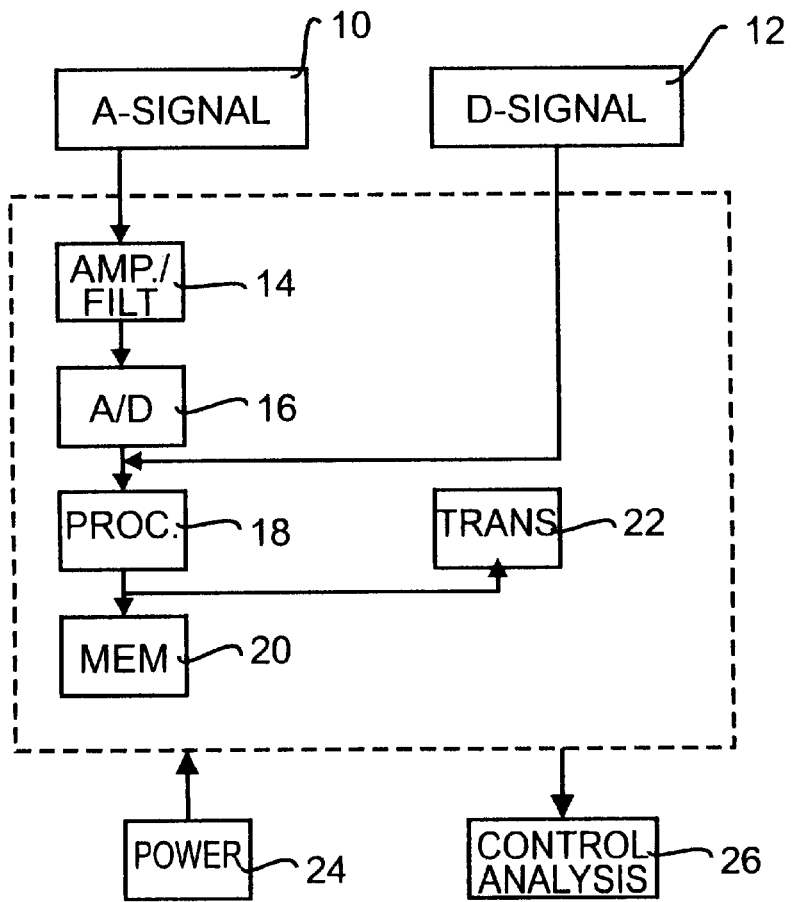
FIG. 2 is a schematic diagram of a unit for collecting and analysing data.

In FIG. 2 a schematic block diagram of the unit 1 is shown. Thus, the unit 1 comprises an input terminal 10 for analogue signals and an input terminal 12 for digital signals. The analogue input terminal is connected to a unit 14 wherein the signal is amplified and filtered. The output signal from the unit 14 is fed to an A/D-converter 16 wherein the signal from the unit 14 is converted into a digital format.

The output signal from the A/D-converter is fed to a computation and control unit 18. The signals input at the terminal 12 are also connected to the unit 18. The unit 18 is connected to a memory 20 in which information can be stored and from which the unit 18 can read information. The unit 18 is also connected to a unit 22 arranged to transmit and receive information from outside the unit 1. The unit 22 can for example be a wireless modem or another suitable interface.

The unit 1 can further comprise a power supply unit 24, for example a rechargeable or replaceable battery. In a preferred embodiment the power supply unit comprises a back-up function so that a battery can be charged or replaced without having to interrupt an ongoing measurement.

The unit 1 may also have an input terminal 26 to which equipment for control, calibration or analysis of the unit 1 can be connected.

Figure 3:
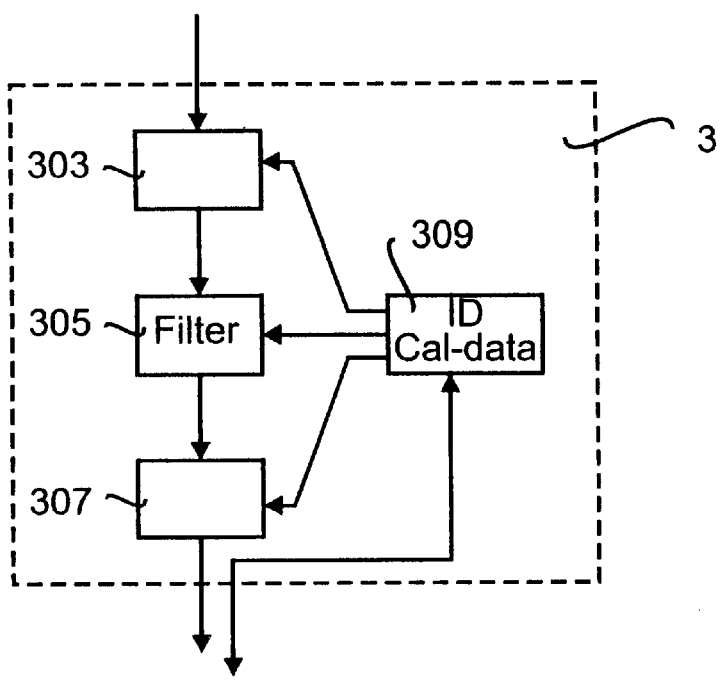
FIG. 3 is a schematic diagram of a preamplifier used in the medical measuring system shown in FIG. 1.

In FIG. 3, a schematic block diagram of the pre-amplifier 3 is shown. Thus, the pre-amplifier 3 comprises a first amplifier 303, which is connected to a number of input terminals arranged to receive plug-in contacts for electrodes, which are attached to a person from whom measured data are collected.

The amplifier 303 is connected to a digital filter 305. The filter 305 filters the signals using a suitable filter. The filter may by different for different types of signals as described below.

The filter 105 is in turn connected to a second amplifier 307 wherein the signals are amplified a second time to a suitable output amplitude. The amplifier 307 is connected to an output terminal through which the pre-amplifier 3 can be connected to the unit 1. The pre-amplifier 3 can also be equipped with a wireless interface towards the unit 1. If such an arrangement is employed the need for cables and input/output terminals can be dispensed with.

Furthermore, the pre-amplifier 3 comprises an identification and calibration unit 309. The unit 109 can communicate with the unit 1 or with another external unit via a bi-directional data communication line. Thus, the unit 1 can read a unique ID-number and also, in a preferred embodiment, read calibration data stored in the unit 109.

In a preferred embodiment the ID-number and the calibration data can be read continuously or every time the pre-amplifier is connected to the unit 1.

IN another preferred embodiment the pre-amplifier 3 can be informed of which type of signal which is to be measured. This is accomplished by means of a special protocol, which informs the pre-amplifier that a particular type of signals are to be measured, for example heart or brain signals.

Since the pre-amplifier is informed of which type of signals that are to be measured the filter 105 can be adjusted for that type of signals and also the amplifiers 103 and 107 can be set to levels, which are suitable for the type of signals to be measured.

Since each pre-amplifier 3 is given a unique identity the unit 1 can sense if the correct pre-amplifier has been connected to the corresponding input terminal of the unit 1. If this is not the case, the unit 1 can correct the mistake or give a signal informing the user of his/her mistake.

Furthermore, since the unit 1 and/or the pre-amplifier 3 has knowledge of which type of signal that is to be measured, an alarm signal can be issued if the wrong type of signal is measured.

Figure 4:
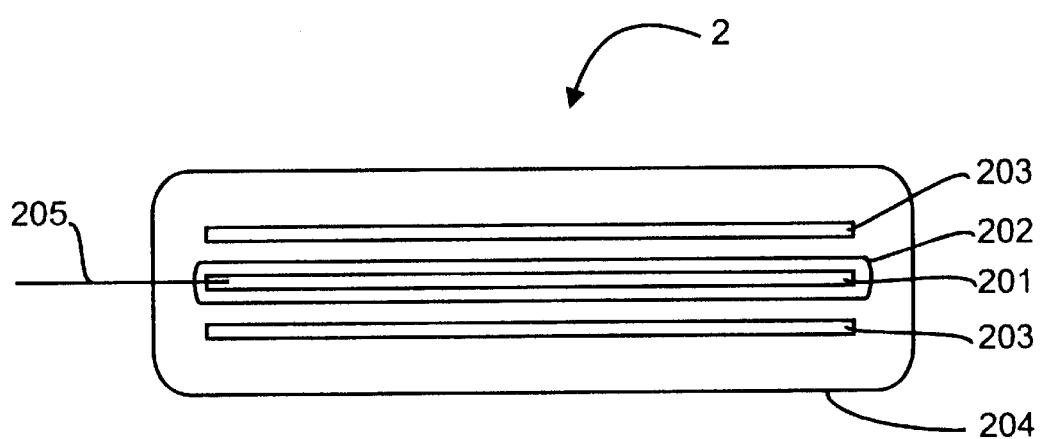
FIG. 4 is a section through a measuring pad for use together with the medical measuring system shown in FIG. 1.

In FIG. 4, a section through the measuring pad 2 is shown. The pad 2 comprises a pressure sensitive element 201 made of a material such as a PVF-film or another type of film, which generates an electrical voltage in response to physical movements or pressure changes. Around the element 201 a protective coating 202 is arranged.

The coating 202 isolates the element 201 from static voltages and other electrical noise. The pad 2 is preferably further provided with a shock absorbing material 203, which protects the element 201 from impacts. The material 203 is preferably a rubber material or another suitable flexible and robust material.

The pad 1 has an outer coating made of a water resistant material 204, which prevents liquid from getting into contact with the pressure sensitive element 201. The element 201 can further communicate with the unit I via a cable 205, which is connected to the unit 1 and to the element 201. The cable 205 is passed through the outer coating 204 of the pad 2 through a watertight passage.

In another preferred embodiment the interface between the unit 1 and the pad 2 is wireless. The element 201 then emits signals to the unit 1 via a wireless modem or via infrared (IR) light, or in any other suitable manner.

A portable system as described herein can be made of very low weight and the measuring parts of the system, i.e. the electrodes and its pre-amplifier(s), and the measuring pad, are therefore easy to bring along when a patient using them wants to move around. This gives the patient much more freedom than what can be achieved with the prior art.

What is claimed is:

1. A portable medical measuring system comprising:
    a plurality of sensors for measuring a plurality of physiological parameters of a patient;
    a data-collecting unit connected to the sensors for receiving signals from the sensors;
    said sensors and data collection unit being portable and mountable to a patient's body and easily carried around by the patient; and
    a remote surveillance unit located at a distance from the data-collecting unit and communicating over a bi-directional communication path with the data-collecting unit, a memory in the data-collecting unit accessible from the remote surveillance unit, the memory collecting physiological data from the patient over a long term and storing data regarding a plurality of the physiological parameters sensed.

2. A system as recited in claim 1 wherein at least one of said sensors measures respiration.

3. A system as recited in claim 1 wherein at least one of said sensors measure brain activities.

4. A system as recited in claim 1 wherein said surveillance unit transmits control signals to said data collecting unit for controlling said data collecting unit to change the physiological parameters being collected by the data collecting unit.

5. A system as recited in claim 1 further comprising at least one physical parameter sensor, and wherein said data collecting unit collects data regarding at least one physical parameter from said at least one physical parameter sensor.

6. A system as recited in claim 1 wherein said sensors and data collecting unit are mounted on the patient, and wherein said system continuously monitors the movements and location of the patient.

7. A system as recited in claim 1 further comprising a signal amplifier device interconnected between at least one of said sensors and said data-collecting unit, said signal amplifier device having an identification circuit for automatic identification of said amplifier to said data-collecting unit.

8. A system as recited in claim 7 wherein said signal amplifier device is capable of storing calibration data.

9. A system as recited in claim 7 wherein said amplifier device comprises a signal filter, the parameters of which can be controlled in response to control signals from said data collecting unit.

10. A system as recited in claim 1 further comprising a pressure sensitive element made of a film which converts pressure changes into an electrical signal, said pressure sensitive element operatively connected to said data collection unit.

11. A system as recited in claim 10 further comprising a shock absorbing elastic material disposed around said film of said pressure sensitive element.

12. A system as recited in claim 11 wherein said shock absorbing elastic material comprises rubber.

13. A system as recited in claim 10 wherein said film comprises polyvinyl fluoride.

14. A system as recited in claim 1 further comprising a measuring pad, said measuring pad comprising a pressure sensitive element, a protective coating surrounding said pressure sensitive element and electrically isolating said pressure sensitive element, and a shock absorbing material encapsulating said protective coating.

15. A system as recited in claim 14 wherein said shock absorbing material comprises rubber.

16. A portable medical measuring system comprising:
    a plurality of sensors for measuring a plurality of physical parameters of a patient;
    a data-collecting unit connected to the sensors for receiving signals from the sensors;
    said sensors and data collection unit being portable and mountable to a patient's body and easily carried around by the patient; and
    a remote surveillance unit located at a distance from the data-collecting unit and communicating over a bi-directional communication path with the data-collecting unit, a memory in the data-collecting unit accessible from the remote surveillance unit, the memory collecting physical data from the patient over a long term and storing data regarding a plurality of the physical parameters sensed.

17. A system as recited in claim 16 wherein said sensors include at least one sensor for sensing body movements of the patient, said data collecting unit collecting data relating to body movements of the patient.

18. A measuring pad comprising:
    a pressure sensitive element,
    a protective coating surrounding the pressure sensitive element, electrically isolating the pressure sensitive element, and
    a shock absorbing material encapsulating the protecting coating.

19. A pad as recited in claim 18 wherein the shock absorbing material is a rubber material.

20. A portable medical data unit comprising:

a plurality of input terminals for sensors provided for measuring physiological parameters of a patient, a communication device for communicating over a bi-directional communication path with a remote surveillance unit located at a distance from the data-collecting unit;

a memory in the data-collecting unit accessible from the remote surveillance unit, the memory collecting physiological data from the patient over a long term and storing data regarding a multitude of physiological parameters from said input terminals; and said portable medical data collecting unit dimensioned and configured to be mounted to a patient's body and easily carried around by the patient.

21. A unit as recited in claim 20 wherein said memory collects data relating to respiration.

22. A unit as recited in claim 20 wherein said memory collects data relating to brain activities.

23. A unit as recited in claim 20 wherein said unit receives control signals from a remote surveillance unit, and changes physiological parameters being collected in response to said control signals.

24. A unit as recited in claim 20 wherein said memory further collects data regarding physical parameters.

25. A unit as recited in claim 20 wherein said unit continuously monitors a location of a patient on whom said unit is mounted.

* * * * *